(12) United States Patent
Yu et al.

(10) Patent No.: US 11,306,310 B2
(45) Date of Patent: Apr. 19, 2022

(54) MICRORNA INHIBITOR

(71) Applicant: SHANGHAI EAST HOSPITAL, Shanghai (CN)

(72) Inventors: Zuoren Yu, Shanghai (CN); Zhongmin Liu, Shanghai (CN); Qian Zhao, Shanghai (CN)

(73) Assignee: SHANGHAI EAST HOSPITAL, Shanghai (CN)

( * ) Notice: Subject to any disclaimer, the term of this patent is extended or adjusted under 35 U.S.C. 154(b) by 0 days.

(21) Appl. No.: 16/319,766

(22) PCT Filed: Jul. 19, 2017

(86) PCT No.: PCT/CN2017/093548
§ 371 (c)(1),
(2) Date: Jan. 22, 2019

(87) PCT Pub. No.: WO2018/014848
PCT Pub. Date: Jan. 25, 2018

(65) Prior Publication Data
US 2020/0071697 A1 Mar. 5, 2020

(30) Foreign Application Priority Data

Jul. 19, 2016 (CN) .......................... 201610570758.8

(51) Int. Cl.
*C12N 15/113* (2010.01)

(52) U.S. Cl.
CPC ...... *C12N 15/113* (2013.01); *C12N 2310/113* (2013.01); *C12N 2310/141* (2013.01); *C12N 2310/3231* (2013.01); *C12N 2310/33* (2013.01)

(58) Field of Classification Search
None
See application file for complete search history.

(56) References Cited

U.S. PATENT DOCUMENTS

| | | | |
|---|---|---|---|
| 2009/0099034 A1* | 4/2009 | Ahlquist .............. | C12Q 1/6809 506/9 |
| 2010/0209487 A1* | 8/2010 | Quay .................... | A61K 47/66 424/450 |
| 2013/0171242 A1* | 7/2013 | Lim ...................... | A61P 35/00 424/450 |
| 2016/0215316 A1* | 7/2016 | Pedersen ............ | C12N 15/1027 |

FOREIGN PATENT DOCUMENTS

| | | | |
|---|---|---|---|
| CN | 101842381 A | 9/2010 | |
| CN | 102325534 A | 1/2012 | |
| CN | 104271742 | * 1/2015 | |
| CN | 104271742 A | 1/2015 | |
| CN | 105132424 A | 12/2015 | |
| WO | WO-2013040429 A1 | * 3/2013 | ........... C12N 15/113 |

OTHER PUBLICATIONS

Ebert et al. Nature Methods 4: 721-726 (Year: 2007).*
Meng, L. et al., "Small RNA Zippers Lock miRNA Molecules and Block miRNA Function in Mammalian Cells", Nature Communications, vol. 8, Jan. 3, 2017 (Jan. 3, 2017), pp. 1-10.
Nassirpour, R. et al., "miR-221 Promotes Tumorigenesis in Human Triple Negative Breast Cancer Cells", PLOS ONE, vol. 8, No. 4, Apr. 24, 2013 (Apr. 24, 2013).
Xia, Xin et al., "Study of miRNA Silencing Mediated by Antisense Oligonucleotide", Journal of Anhui Agricultural Sciences, vol. 39, No. 24, Dec. 31, 2011 (Dec. 31, 2011), pp. 14545-14547.
Yaman, I. et al., The Zipper Model of Translational Control: A Small Upstream ORF Is the Switch that Controls Structural Remodeling of an mRNA Leader, Cell, vol. 113, May 16, 2003 (May 16, 2003), pp. 519-531.

* cited by examiner

*Primary Examiner* — Brian Whiteman
(74) *Attorney, Agent, or Firm* — Muncy, Geissler, Olds & Lowe, P.C.

(57) ABSTRACT

A microRNA (miRNA) inhibitor, being able to form a stable DNA-RNA double-stranded structure with a miRNA. The double-stranded structure comprises: (i) a miRNA unit sequence, and (ii) an RNA zipper unit sequence. The 5'-end of the RNA zipper unit sequence is connected to the 5'-end of the miRNA unit sequence. The 3'-end of the RNA zipper unit sequence is connected to the 3'-end of the miRNA unit sequence. The RNA zipper can connect the head of the miRNA molecule to the tail of the miRNA molecule to form a stable long-chain structure. The RNA zipper unit sequence contains 1-3 nucleotides not connected to the miRNA unit sequence. The DNA-RNA double-stranded structure can be used to inhibit biological activities of a miRNA unit, does not have biological toxicity, and has the advantages of high affinity, high specificity and high stability.

7 Claims, 6 Drawing Sheets
Specification includes a Sequence Listing.

SEQUENCE LISTING

<160> NUMBER OF SEQ ID NOS: 8

<210> SEQ ID NO 1
<211> LENGTH: 24
<212> TYPE: DNA
<213> ORGANISM: Artificial sequence
<220> FEATURE:
<223> OTHER INFORMATION: RNA zipper unit sequence

<400> SEQUENCE: 1
aatgtagcta gaaacccagc agac                      24

<210> SEQ ID NO 2
<211> LENGTH: 24
<212> TYPE: DNA
<213> ORGANISM: Artificial sequence
<220> FEATURE:
<223> OTHER INFORMATION: RNA zipper unit sequence

<400> SEQUENCE: 2
aagcactttg gctacctgca ctgt                      24

<210> SEQ ID NO 3
<211> LENGTH: 23
<212> TYPE: DNA
<213> ORGANISM: Artificial sequence
<220> FEATURE:
<223> OTHER INFORMATION: RNA zipper unit sequence

<400> SEQUENCE: 3
ctactacctc acaactatac aac                       23

<210> SEQ ID NO 4
<211> LENGTH: 23
<212> TYPE: DNA
<213> ORGANISM: Artificial sequence
<220> FEATURE:
<223> OTHER INFORMATION: RNA zipper unit sequence

<400> SEQUENCE: 4
aatgtagctg aaacccagca gac                       23

<210> SEQ ID NO 5
<211> LENGTH: 23
<212> TYPE: DNA
<213> ORGANISM: Artificial sequence
<220> FEATURE:
<223> OTHER INFORMATION: RNA zipper unit sequence

<400> SEQUENCE: 5
aagcactttg ctacctgcac tgt                       23

<210> SEQ ID NO 6
<211> LENGTH: 23
<212> TYPE: RNA
<213> ORGANISM: Homo sapiens

```
<400> SEQUENCE: 6
caaagugcuu acagugcagg uag                                       23

<210> SEQ ID NO 7
<211> LENGTH: 23
<212> TYPE: RNA
<213> ORGANISM: Homo sapiens

<400> SEQUENCE: 7
agcuacauug ucugcugggu uuc                                       23

<210> SEQ ID NO 8
<211> LENGTH: 22
<212> TYPE: RNA
<213> ORGANISM: Homo sapiens

<400> SEQUENCE: 8
ugagguagua gguuguauag uu                                        22
```

MICRORNA INHIBITOR

TECHNICAL FIELD

The present invention relates to the field of biology, and in particular to a small RNA inhibitor, and more particularly to a stable DNA-RNA double-stranded structure formed by binding of a small RNA inhibitor to a small RNA.

BACKGROUND

Thousands of miRNA sequences have been discovered and predicted in eukaryotic cells. More and more evidences show that miRNAs are closely related to diseases and that miRNA expression is abnormal in many diseases including cancer.

Among thousands of miRNA molecules, only some miRNA molecules' function are clear, the regulatory functions of most miRNAs in vivo, as well as their relationship with diseases, are unknown.

Many miRNA molecules have been shown to be pathogenic miRNAs, such as miR-21 which can promote tumorigenesis. Specifically reducing the expression levels of these miRNAs, or specifically blocking their biological functions, is considered as a gene therapy having clinical application prospects. Currently, chemically modified miRNA inhibitors are widely used, and modifications include the addition of 2'-O methylation, a 2'-O-binding 4'-C methylene bridge to form high-affinity RNA-locked nucleic acid structures, and the like. Chemically modified miRNA inhibitors have enhanced binding capacity to miRNAs, however, the efficacy and persistence of blocking the function of miRNA are the gold standard for evaluating miRNA inhibitors. Commonly used miRNA inhibitors include:

a) Antisense miRNA oligonucleotide (anti-miRNA oligonucleotide, AMO) is a single-stranded molecule consisting of 17 to 22 nucleotides, often accompanied by chemical modification. A typical modification is 2'-O-methyl group modification. AMO can directly inhibit a particular miRNA, that is, binding to the target miRNA through the principle of base pairing, and then specifically inhibiting its function. Antisense oligonucleotides have a limited effect on knockdown of miRNA gene expression, and the duration of action is not long.

b) Locked nucleic acid (LNA) is a product of LNA modification on ASO. The so-called LNA technique refers to the formation of high affinity by introducing a 2'-O, 4'-C methylene bridge. The mechanism of action of LNA antisense miRNAs is identical to that of ASO and AMO, but it has the advantages of high stability and higher target-specific affinity.

c) miRNA-sponge (miRNA sponge) carrying a gene sequence with multiple binding sites for miRNA. After being introduced into a cell, it is transcribed with the vector gene, and the sequence occupies the endogenous miRNA in the cell with a high affinity, thereby blocking the binding of the target gene and the miRNA. The disadvantages are limited effects, complicated mechanism, unstable effects and high cost.

d) miRNA barrier (miR-Mask), which is a small molecule sequence 100% complementary to the target gene binding site of the miRNA, and can theoretically bind to the target gene with higher complementarity and affinity, preferentially occupying the binding site of the target gene, blocking the binding of an endogenous miRNA to the target gene. The disadvantage is that its inhibition effects are unstable and limited, and the adjustment mechanism is complicated, so that this method is not widely used.

Therefore, there is an urgent need in the art to develop new, stable miRNA inhibitors.

SUMMARY OF THE INVENTION

The object of the present invention is to provide a small RNA inhibitor with a stable and long-lasting effect.

In the first aspect of the present invention, it provides a stable DNA-RNA double-stranded structure, and the double-stranded structure comprises:

(i) a miRNA unit sequence, the number of the miRNA unit is p, and (ii) a RNA zipper unit sequence, the number of the RNA zipper unit is g, wherein each RNA zipper unit sequence is single-stranded, and the 5' end of each RNA zipper unit sequence binds to the 5' end of the miRNA unit sequence, and the 3' end of each RNA zipper unit sequence binds to the 3' end of the miRNA unit sequence, and there are consecutive 0-3 nts in the RNA zipper unit sequence not binding to the miRNA unit sequence;

and p and g are positive integers, $p+g \geq 3$, and $|p-g| \leq 1$.

In another preferred embodiment, the double-stranded structure is non-naturally occurring, and/or artificially synthesized.

In another preferred embodiment, there are consecutive 1-2 nts in the RNA zipper unit sequence not binding to the miRNA unit sequence.

In another preferred embodiment, the RNA zipper unit sequence is a DNA sequence.

In another preferred embodiment, the $s=p+g$, and s is a positive integer of 3-1000000, and/or a positive integer of 3-100,000, and/or a positive integer of 3-10000, and/or a positive integer of 3-1000, and/or a positive integer of 3-100, and/or a positive integer of 3-10.

In another preferred embodiment, the $s=p+g$ and s is an odd number.

In another preferred embodiment, a region where the 5' end of the RNA zipper unit sequence binds to the 5' end of the miRNA unit sequence is the first binding region, and the ratio R1 of the length N1 of the first binding region to the length N0 of the RNA zipper unit sequence is (0.8–1.2):2.0.

In another preferred embodiment, a region where the 3' end of the RNA zipper unit sequence binds to the 3' end of the miRNA unit sequence is the second binding region, and the ratio R2 of the length N2 of the second binding region to the length N0 of the RNA zipper unit sequence is (1.2–0.8):2.0.

In another preferred embodiment, the ratio R3 of the length N1 of the first binding region to the length N2 of the second binding region is (0.4–0.6):(0.6–0.4).

In another preferred embodiment, the first binding region and the second binding region do not overlap.

In another preferred embodiment, the first binding region and the second binding region in the RNA zipper unit sequence are separated by 0-3 nts.

In another preferred embodiment, the first binding region and the second binding region in the RNA zipper unit sequence are separated by 1 nt.

In another preferred embodiment, the first binding region and the second binding region in the sequence of the RNA zipper unit are separated by one guanine (G) or one thymine (T).

In another preferred embodiment, the first binding region and the second binding region in the miRNA unit sequence are separated by 0-3 nts.

In another preferred embodiment, the first binding region and the second binding region in the miRNA unit sequence are separated by 1 nt.

In another preferred embodiment, each miRNA unit sequence is separated by 0-3 nts.

In another preferred embodiment, each RNA zipper unit sequence is separated by 0-3 nts.

In another preferred embodiment, each RNA zipper unit sequence is identical.

In another preferred embodiment, the miRNA unit is selected from the group consisting of:
miRNA, siRNA, and piRNA.

In another preferred embodiment, the miRNA comprises an endogenous miRNA and an exogenous miRNA.

In another preferred embodiment, the miRNA comprises a pathogenic miRNA.

In another preferred embodiment, the miRNA is selected from the group consisting of: miR-17, miR-221, and let-7a.

In another preferred embodiment, the RNA zipper unit sequence contains an LNA modified base.

In another preferred embodiment, the length of the RNA zipper unit sequence is greater than or equal to 19 nt, preferably 19-26 nt.

In another preferred embodiment, the length of the miRNA unit sequence is greater than or equal to 18 nt, preferably 18-23 nt.

In another preferred embodiment, the RNA zipper unit inhibits biological functions of the miRNA unit.

In another preferred embodiment, the sequence of the RNA zipper unit inhibiting miR-221 is shown in SEQ ID NO.: 1.

In another preferred embodiment, the sequence of the RNA zipper unit inhibiting miR-17 is shown in SEQ ID NO.: 2.

In another preferred embodiment, the sequence of the RNA zipper unit inhibiting let-7a is shown in SEQ ID NO.: 3.

In the second aspect of the present invention, it provides a use of the DNA-RNA double-stranded structure of the first aspect of the present invention for inhibiting biological functions of the miRNA unit.

In the third aspect of the present invention, it provides a method of forming a DNA-RNA double-stranded structure according to the first aspect of the present invention, comprising the steps of:

(i) contacting the RNA zipper unit sequence with the miRNA unit sequence, thereby forming the DNA-RNA double-stranded structure according to the first aspect of the present invention.

In another preferred embodiment, the method is an in vitro method.

In another preferred embodiment, the method is a non-therapeutic and non-diagnostic method.

In the fourth aspect of the present invention, it provides a pharmaceutical composition comprising: (a) an RNA zipper unit sequence for forming the DNA-RNA double-stranded structure according to the first aspect of the present invention and b) a pharmaceutically acceptable carrier.

In another preferred embodiment, the pharmaceutical composition is used for inhibiting a miRNA unit sequence binding to the RNA zipper unit sequence.

In the fifth aspect of the present invention, it provides a use of an RNA zipper unit sequence for the preparation of a pharmaceutical composition for inhibiting miRNA, and the RNA zipper unit sequence and the miRNA can form the DNA-RNA double-stranded structure according to the first aspect of the present invention.

In the sixth aspect of the present invention, it provides a small RNA inhibitor comprising a first binding region and a second binding region; the first binding region is located at 5' end of the small RNA inhibitor, comprising an antisense complementary sequence targeting a 5' region of a small RNA, which can bind to the 5' region of the targeted small RNA molecule by base complementation; the second binding region is located at 3' end of the small RNA inhibitor, comprising the same antisense complementary sequence targeting the 3' region of the small RNA, which can bind to the 3' region of the targeted small RNA molecule by base complementation.

The 5' region of the targeted small RNA refers to a region located at the 5' end of the targeted small RNA, which binds to the first binding region of the small RNA inhibitor.

The 3' region of the targeted small RNA refers to a region located at the 3' end of the targeted small RNA, which binds to the second binding region of the small RNA inhibitor.

The "binding by base complementation" means that the first binding region or the second binding region contains a base which can be paired by base complementation to the base of the 5' region or the 3' region of the targeted small RNA: In a preferred embodiment, the base of the first binding region or the second binding region may completely complementation-bind to the base of the 5' region or the 3' region of the targeted small RNA; in another preferred embodiment, the base of the first binding region or the second binding region may partially complementation-bind to the base of the 5' region or the 3' region of the targeted small RNA; in order to achieve stable and specific base complementary binding, the number of partially complementation-binding bases is not less than 90% of the total number of bases in the region.

In another preferred embodiment, the partially complementation-binding is such that at most two bases in the first binding region or the second binding region are unable to form a base pair with a corresponding position of the targeted small RNA. The base that cannot form a base pair may be located at a free end or within a chain of the first binding region or the second binding region; when a base that cannot form a base pair is present within the chain, a bulge or bubble may be formed in the double-stranded structure as described in the first aspect of the present invention.

In another preferred embodiment, the partially complementation-binding is a deletion of at most two bases in the first binding region or the second binding region, and the deleted base may be located in the free end or within the chain of the first binding region or the second binding region; when a deleted base is present in the chain, a bulge or bubble is formed in the double-stranded structure as described in the first aspect of the present invention.

In another preferred embodiment, the first binding region contains a nucleotide chain in a length of N1 (chain length is the number of nucleotides or bases, and the chain lengths described below are all the numbers of nucleotides or bases). The second binding region contains a nucleotide chain in a length of N2, and the 5' region of the targeted small RNA has a nucleotide chain in a length of N1', and the 3' region of the targeted small RNA has a nucleotide chain in a length of N2', the nucleotide length of the targeted small RNA is N0, and the 5' region of the targeted small RNA does not overlap with the 3' region of the targeted small RNA, wherein $N1'+N2'=N0;$ $0.3<N1'/N0<0.7;$ $0.3<N2'/N0<0.7;$ $N1:N0=(0.3\sim0.7):1;$ $N2:N0=(0.3\sim0.7):1.$ In another preferred embodiment, N1:N0=(0.4–0.6):1, N2:N0=(0.4–0.6): 1.

In another preferred embodiment, N1/N0+N2/N0=1.

In another preferred embodiment, the bases of the first binding region or the second binding region are completely complementation-paired to the bases of the 5' region or the 3' region of the targeted small RNA, i.e., the bases of the first binding region or the second binding region are 100% complementation-paired to those of the 5' region or the 3' region of the targeted small RNA.

In another preferred embodiment, the number of bases in the first binding region which are complementary to the 5' region of the targeted small RNA is not less than 90% of the number of nucleotides of the first binding region; The number of bases in the second binding region which are complementary to the 3' region of the targeted small RNA is not less than 90% of the number of nucleotides of the second binding region In a preferred embodiment, there is a junction region between the first binding region and the second binding region.

In another preferred embodiment, the junction region and the first binding region and the second binding region are single-stranded.

In another preferred embodiment, the junction region comprises 0-3 nucleotide residues or non-nucleotide residues similar in steric hindrance to the 0-3 nucleotide residues; the junction region comprising 0 nucleotide residue means that the first binding region and the second binding region are directly linked by a phosphoester bond of a nucleotide residue; the non-nucleotide residue refers to chemical residues other than nucleotide residues or phosphoester bonds, including, but are not limited to, amino acid residues, amide groups, hydrocarbyl groups, ether groups, oligosaccharyl, and the like.

In another preferred embodiment, the junction region comprises one nucleotide residue selected from the group consisting of: adenine (A), thymine (T), uracil (U), guanine (G) and cytosine (C).

More preferably, the nucleotide residue of the junction region is G or T.

In a preferred embodiment, the junction region comprises an antisense complementary sequence of n small RNA molecules, and the small RNA molecule is identical to the small RNA targeted by the first binding region or the second binding region. The junction region also can bind and target the small RNA molecule, thereby inhibiting biological functions of the targeted small RNA.

In another preferred embodiment, the junction region comprises an antisense complementary sequence of n small RNA molecules, and the small RNA molecule is different from the small RNA targeted by the first binding region or the second binding region. The junction region may comprise an antisense complementary sequence of a plurality of small RNA molecules, and has the function of inhibiting functions of a plurality of small RNA molecules.

In another preferred embodiment, the junction region is double-stranded, and the double-stranded junction region is derived from the combination of the antisense complementary sequences of the first binding region and the second binding region.

In another preferred embodiment, the double-stranded junction region comprises at least 7 base pairs.

In a preferred embodiment, the nucleotide residues of the first binding region and the second binding region contain modified bases.

In another preferred embodiment, the modified base includes, but is not limited to, LNA, 2'-OMe, 2'-MOE, 2'-Fluoro, PNA, morpholino, ZEN or GalNac.

In another preferred embodiment, the sequence of the small RNA inhibitor is as shown in SEQ ID NO.: 1.

In another preferred embodiment, the sequence of the small RNA inhibitor is as shown in SEQ ID NO.: 2.

In another preferred embodiment, the sequence of the small RNA inhibitor is as shown in SEQ ID NO.: 3.

In the seventh aspect of the invention, it provides a use of the small RNA inhibitor according to the sixth aspect of the present invention for the preparation of a pharmaceutical composition for inhibiting a small RNA or inhibiting biological functions of a small RNA.

In the eighth aspect of the present invention, it provides a method for forming the DNA-RNA double-stranded structure according to the first aspect of the present invention, comprising the steps of:

(i) mixing the small RNA inhibitor according to the sixth aspect of the present invention or the RNA zipper unit sequence according to the first aspect of the present invention with the small RNA unit sequence, thereby forming the DNA-RNA double-stranded structure according to the first aspect of the present invention.

In the ninth aspect of the present invention, it provides a pharmaceutical composition comprising: (a) a small RNA inhibitor according to the sixth aspect of the present invention and (b) a pharmaceutically acceptable carrier.

In the tenth aspect of the present invention, it provides a kit comprising: (a) an RNA zipper unit sequence for forming the DNA-RNA double-stranded structure according to the first aspect of the present invention or a small RNA inhibitor according to the sixth aspect of the present invention and (b) a biologically acceptable carrier.

In the eleventh aspect of the present invention, it provides a stable chain structure, comprising:

(i) a small RNA unit sequence, the number of the small RNA unit is p, and (ii) a small RNA inhibitor unit sequence, the number of the small RNA inhibitor unit is g, wherein the small RNA unit sequence and the small RNA inhibitor unit sequence are combined into a chain structure by base complementation, p and g is a positive integer, and p+g≥3.

In another aspect of the present invention, the following is also provided:

1. The microRNA zipper can specifically inhibit the binding of the target microRNA to the target gene, and block its biological functions, and have the effect of intracellular gene knockdown;

2. Structural design of microRNA zippers can connect the target microRNA molecules end to end to form an RNA-DNA double-stranded structure;

3. 1-3 additional bases are designed in the middle of the zipper molecule to allow sufficient space between the target microRNA molecules to form a more stable DNA-RNA double strand;

4. In order to avoid the self-binding of microRNA zippers and enhance the binding specificity between microRNA zippers and target miRNAs, locked nucleic acid (LNA) technology is used to synthesize microRNA zippers.

5. The microRNA zipper at a concentration of 20-80 nM has the best effect on inhibiting the target miRNA;

6. The microRNA zipper can be used not only for miR-NAs, but also for other microRNAs, including specific inhibition on piRNAs and endogenous siRNAs;

7. MicroRNA zippers have the potential to be clinically used in the target-inhibition on pathogenic microRNAs;

8. MicroRNA zippers have the advantage of combining high affinity, high specificity and high stability with targeted miRNAs; It should be understood that, within the scope of the present invention, each technical feature of the present invention described above and in the following (as examples) may be combined with each other to form a new or preferred technical solution, which is not listed here due to space limitations.

DESCRIPTION OF FIGURE

In FIG. 1, element B shows that the microRNA zipper in one embodiment connects a target microRNA molecule end to end to form a stable double-stranded structure.

In FIG. 15, element B shows the binding mode of a double-stranded microRNA zipper to a target microRNA in one embodiment.

DETAILED DESCRIPTION

Figure 1:
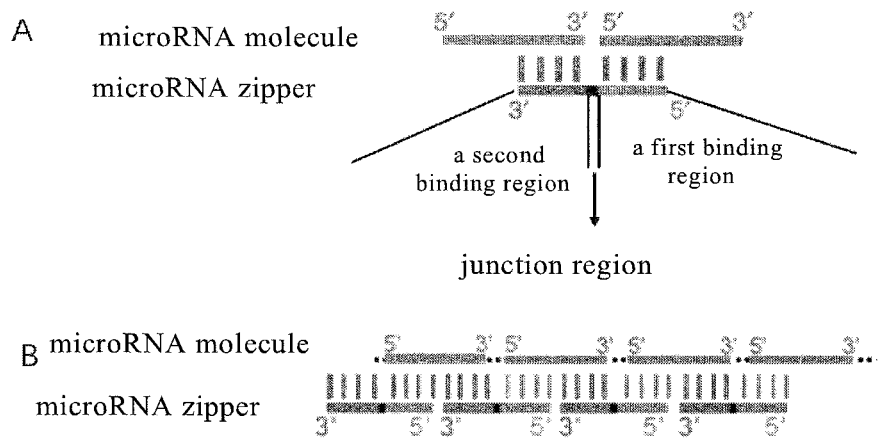
In FIG. 1, element A shows a structure of a microRNA zipper (microRNA inhibitor) in an embodiment, wherein the sequence at the 5' end is the first binding region, and the sequence at the 3' end is the second binding region, the first binding region and the second binding region are connected by an intermediate junction region, the first binding region can be combined with the region at the 5' end of the microRNA molecule by means of base complementation, and the second binding region can be combined with the region at the 3' end of the microRNA molecule by means of base complementation.

After an extensive and in-depth study, the present inventors have unexpectedly discovered that a microRNA inhibitor can form a stable double-stranded-like structure with a target microRNA by base complementation and the double-stranded structure includes (i) a miRNA unit sequence (targeted microRNA), and (ii) an RNA zipper unit sequence (microRNA inhibitor), wherein the 5' end of the RNA zipper unit sequence binds to the 5' end of the miRNA unit sequence, the 3' end of the RNA zipper unit sequence binds to the 3' end of the miRNA unit sequence. Experiments show that each RNA zipper unit forms a stable double-stranded structure by ligating the miRNA unit sequences end to end, which can effectively inhibit biological activities of the miRNA unit, and has the advantages of high affinity, high specificity and high stability.

Terms

As used herein, the terms "microRNA zipper", "microRNA zipper", "RNA zipper unit", "small RNA inhibitor" and "microRNA inhibitor" can be used interchangeably, referring to a short-stranded nucleic acid sequence capable of binding and inhibiting microRNAs.

miRNAs are a class of factors that modulate gene expression by complementary base pairing with the target mRNAs after the transcription. The function of most miRNAs remains unclear, and biological methods that explore their function by limiting their expression are widely explored. Previous method for knocking down miRNA expression, including antisense oligonucleotides, miRNA sponges, miRNA barriers, miRNA small molecule inhibitors, and the like. Antisense oligonucleotides have limited effect in inhibiting miRNAs. The miRNA sponges or miRNA barriers specifically knock down the miRNA gene, and it has not been widely used due to its insufficient stability and complex regulatory mechanisms.

The invention utilizes the short feature of the miRNA sequence, and skillfully designs a microRNA zipper, which can connect the microRNAs end to end, and further enhances the stability of the microRNA zipper, ensures the complementary pairing between the microRNA zipper and the microRNA, effectively blocks the binding of the microRNA to the target gene, and thus inhibits the biological function of the microRNA by means of nucleic acid modification technology such as locked nucleic acid (LNA).

At the same time, other types of microRNAs, such as piRNA (Piwi-interacting RNA), a non-coding microRNA of about 24-32 nt in length, or siRNA (Small interfering RNA), a class of double-stranded RNAs that are involved in RNA interference and are about 20-25 nt in length, can all utilize the design of the relevant microRNA zipper to achieve the inhibition on biological functions.

In particular, the present invention establishes a microRNA zipper that binds to a target microRNA with high affinity, high specificity, and high stability, thereby blocking the binding of the microRNA and the target sequence, so that the microRNA function is deleted or inhibited.

In view of the fact that microRNAs are only 18-32 bases, the inventors have skillfully designed a small RNA inhibitor having a first binding region and a second binding region, the first binding region is located at the 5' end of the small RNA inhibitor and contains an antisense complementary sequence that targets the 5' region of the small RNA, which can bind to the 5' region of the targeted small RNA molecule by base complementation; the second binding region is located at the 3' end of the small RNA inhibitor and contains the same antisense complementary sequence that targets the 3' region of the small RNA, which can bind to the 3' region of the targeted small RNA molecule by base complementation. Since a small RNA inhibitor can connect the second half of a small RNA molecule sequence with the first half of another small RNA molecule, it is called a microRNA zipper.

In order to avoid self-complementary structure and improve binding specificity, nucleic acid modification techniques such as locked nucleic acid (LNA) have been applied to the synthesis of microRNA zippers.

MicroRNA zippers have the advantage of binding to targeted microRNAs with high affinity, high specificity and high stability.

As used herein, the terms "microRNA", "small RNA", "targeted small RNA", "miRNA unit sequence" include short RNA strands of 18-32 nts, such as miRNA, siRNA, and piRNA, which are generalized small RNAs (or MicroRNA) sequence.

As used herein, the terms "gap" and "junction region" have the same meaning and refer to a few bases, preferably 1-3 bases, which are placed in the microRNA zipper sequence to connect the first binding region with the second binding region. It can create a small gap between the two targeted miRNA molecules, providing sufficient space for generating a stable nucleic acid structure, which not only benefits the miRNA gene knockdown effect, but also ensures the binding specificity between the microRNA zipper and the target miRNA.

As used herein, the term "miRNA" (microRNA) is a class of non-coding single-stranded RNA molecule of about 20-24 nucleotides in length encoded by an endogenous gene, which is involved in the regulation of expression of a large number of genes in plants and animals. To date, more than 4,000 miRNA molecules have been found in animals, plants and viruses. Most miRNA genes are present in the genome in the form of single copies, multiple copies, or clusters. Each miRNA can regulate multiple target genes, while several miRNAs can also participate together in the regulation of the same gene to form a complex regulatory network. It is speculated that miRNA regulates the expression of more than half of human genes. MiRNA exists in many forms, the most primitive one is pri-miRNA; pri-miRNA is processed by Drosha to become pre-miRNA, i.e., miRNA precursor of about 50-90 nucleotides in length; after the pre-miRNA is digested by Dicer, it becomes a mature miRNA of about 20-24 nucleotides in length. MiRNAs inhibit target gene expression primarily by inhibiting translation and accelerating mRNA de-adenylation, which differs from siRNA-mediated mRNA degradation.

As used herein, the term "RNAi (RNA interference)" refers to a phenomenon that is highly conserved during evolution and is induced by double-stranded RNA (dsRNA), and efficiently and specifically degrades RNA with complementary pairing sequences. Since RNAi technology can specifically shut down the expression of specific genes, this technology has been widely used in the fields such as the exploration of gene function and gene therapy for infectious diseases and tumors. DsRNA-mediated RNAi is found in many eukaryotes such as fungi, *Drosophila, Arabidopsis thaliana*, trypanosomes, leeches, worms, zebrafish, etc., and posttranscriptional gene silencing (PTGS) in plants, cosuppression and RNA-mediated viral resistance, and fungal inhibition (quelling) are also manifestations of RNAi in different species.

As used herein, the term "small interfering RNA (siRNA)" refers to a small RNA molecule (about 21-25 nucleotides) that can be processed from its precursor (such as dsRNA, shRNA, etc.) by Dicer (an enzyme specific for double-stranded RNA in the RNase III family). It can also be synthesized chemically or produced by other protein processing. SiRNA is a major member of siRISC, inspiring target RNA complementary to its sequence to be rapidly cleaved and degraded, resulting in silencing of the target gene, thus becoming a key functional molecule in RNAi.

As used herein, the term "piRNA (Piwi-interacting RNA)" refers to a small RNA molecule (about 24-32 nt) that is mainly found in the reproductive system and the expression of the target gene and the modification at the transcriptional and post-transcriptional levels are performed after binding to the PIWI protein, and specific functions are still under investigation.

As used herein, the term "Locked Nucleic Acid (LNA)" refers to an oligonucleotide-like derivative in which the 2'-O, 4'-C positions of 13-D-ribofuranose form a rigid structure by dehydration.

As used herein, the term "2'-OMe" refers to a 2'-methoxylation modification for increasing the stability of a nucleic acid strand.

As used herein, the term "2'-MOE" refers to a 2'-O-methoxyethyl modified nucleotide.

As used herein, the term "2'-Fluoro" refers to a 2'-fluoro modified nucleotide.

As used herein, the term "PNA" means that a pentose phosphate diester bond skeleton in a ribose nucleic acid is substituted with a peptide chain amide 2-aminoethylglycine bond.

As used herein, the term "morpholino" refers to the modification of an antisense oligonucleotide with a morpholine ring.

As used herein, the term "ZEN" refers to the modification of a nucleotide with N—N-diethyl-4-(4-nitronaphthalen-1-ylazo)-aniline.

As used herein, the term "GalNac" refers to the modification of a nucleotide with an N-acetylgalactosamine (GalNAc).

As used herein, the term "steric hindrance" refers to the steric hindrance caused by the proximity of certain atoms or groups in a molecule and the intramolecular tension caused by the deviation from normal bond angles, therefore, a certain spatial distance is maintained between atoms or groups.

As used herein, the term "double-stranded structure", "double-stranded-like structure", "DNA-RNA double-stranded structure" is a stable double-stranded structure formed by the end-to-end connection between microRNA zipper (DNA or RNA) of the present invention and the microRNA (RNA), thereby inhibiting the biological function of small RNAs. In particular, the double-stranded structure includes:

(i) a miRNA unit sequence, the number of the miRNA unit is p, and (ii) an RNA zipper unit sequence, the number of the RNA zipper unit is g, wherein, each RNA zipper unit sequence is single-stranded, and the 5' end of each RNA zipper unit sequence binds to the 5' end of the miRNA unit sequence, and the 3' end of each RNA zipper unit sequence binds to the 3' end of the miRNA unit sequence, and there are consecutive 0-3 nts in the RNA zipper unit sequence that does not bind to the miRNA unit sequence;

and p and g are positive integers, p+g≥3, and |p−g|≤1.

The main advantages of the present invention include:

(a) The microRNA zipper of the present invention can specifically inhibit the binding of a target microRNA to a target gene, block its biological function, and have an intracellular gene knockdown function.

(b) Structural design of microRNA zipper of the present invention can link target microRNA molecules end to end to form an RNA-DNA double-stranded structure.

(c) The microRNA zipper of the present invention has the advantage of binding to a targeted miRNA with high affinity, high specificity, and high stability.

(d) The microRNA zipper of the present invention has a high sequence specificity for knocking down function of the targeted miRNA, and has no effect on other homologous miRNAs, and has no off-target effect.

The present invention is further described below with reference to specific embodiments. It should be understood that these examples are only for illustrating the present invention and not intended to limit the scope of the present invention. The conditions of the experimental methods not specifically indicated in the following examples are usually in accordance with conventional conditions or the manufacturer's proposed conditions. Unless otherwise indicated, percentages and parts are by weight and parts by weight.

Example 1

MicroRNA Zipper Design

Using the short features of microRNA sequences, a DNA sequence (which is called a microRNA zipper) was designed to target a certain miRNA molecule, wherein the first binding region of the microRNA zipper can bind to the 5' region of the miRNA molecule by base complementation, the second binding region of the microRNA zipper can bind to the 3' region of the miRNA molecule by base complementation. Therefore, each microRNA zipper can be complementary to the latter half of one miRNA molecule sequence and the first half of another miRNA molecule. A miRNA zipper molecule can link two target miRNA molecules end to end. The microRNA zipper structure of the present invention is as shown in FIG. 1A, and the binding mode to the target miRNA is as shown in FIG. 1B.

The composition of the microRNA zipper is not limited to deoxyribonucleic acid, and ribonucleic acid or other types of alternative bases well known in the art can achieve the same effect.

It has been found that the junction region can be designed in the microRNA zipper sequence (FIG. 1A microRNA zipper, black portion). In a preferred embodiment, when 1-3 bases are placed to link the first binding region and the second binding region, a small gap can be created between the two targeted miRNA molecules and a sufficient space was provided for generating a stable nucleic acid structure, which not only benefits the miRNA gene knockdown effect, but also ensures the binding specificity between the microRNA zipper and the target miRNA.

In order to avoid the self-binding of microRNA zippers and enhance the binding specificity between microRNA zippers and target miRNAs, nucleic acid modification techniques such as locked nucleic acid (LNA) were used to synthesize microRNA zippers.

Figure 2:
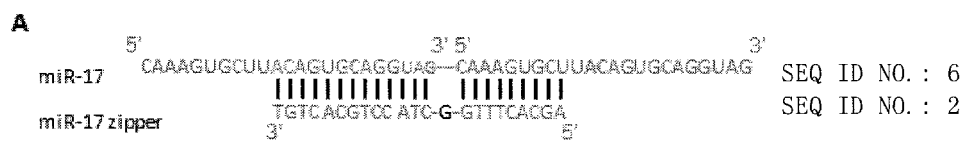
FIG. 2 shows the zipper sequence and structure pattern for microRNA-17 in one embodiment.
Figure 3:
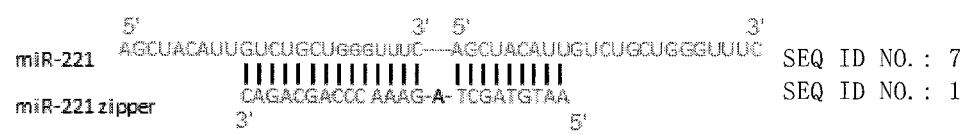
FIG. 3 shows the zipper sequence and structure pattern for microRNA-221 in one embodiment.
Figure 4:
FIG. 4 shows the zipper sequence and structure pattern for microRNA let-7a in one embodiment.

MicroRNA zippers binding to miR-17, miR-221 and let-7a were constructed using Exiqon's LNA™ oligo tools and design guidelines, respectively. FIGS. 2, 3 and 4 show the designed miR-17 zipper, miR-221 zipper and let-7a zipper, respectively.

The miR-17 zipper, miR-221 zipper and let-7a zipper sequence are shown as follows (those with a + sign are LNA modified bases)

miR-221 zipper:
(SEQ ID NO.: 1)
5'AA+TGTAGCTAGAAACCCAGCA+GAC 3';

miR-17 zipper:
(SEQ ID NO.: 2)
5'A+AGCACTTTGGCTACCTGCACT+GT 3';

Let-7a zipper:
(SEQ ID NO.: 3)
5'CTACTACCTCACAACT+ATACA+AC 3';

Example 2

Verification for the MicroRNA Zipper Function and Specificity

To examine the effect of microRNA zippers on target miRNAs, the miR-17 zipper was synthesized, as shown in FIG. 2, and transfected into the breast cancer cell line MDA-AB-231. Fluorescence quantitative PCR reaction was utilized in this protocol to detect the abundance of miR-17 expression in cells before and after transfection of miR-17 zipper.

Figure 5:
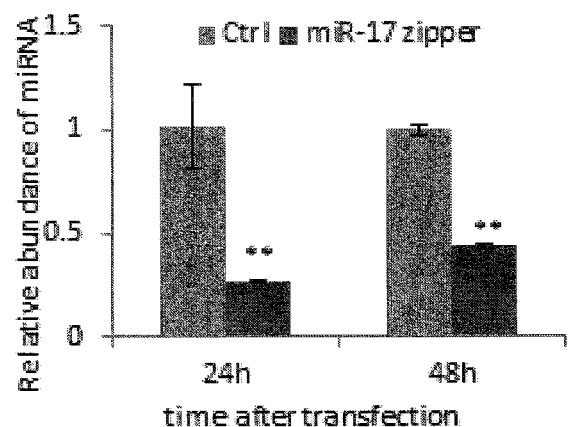
FIG. 5 shows that in one embodiment, the microRNA-17 zipper specifically reduces the expression level of miR-17 in cells.

As shown in FIG. 5, the result showed that the intracellular level of target miRNA-17 was reduced by about 80% after microRNA-17 zipper was transfected into cells at a concentration of 30 nM for 24 hours.

In addition, the effect of miR-221 zipper on the abundance of miR-221 in breast cancer cell line MDA-MB-231 was examined.

Figure 6:
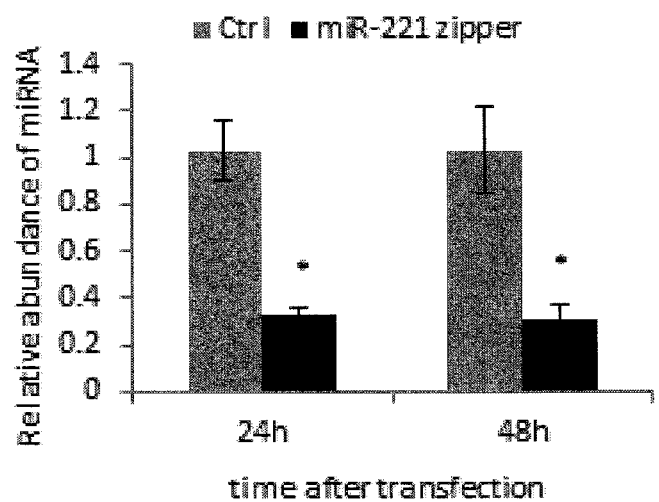
FIG. 6 shows that in one embodiment, the microRNA-221 zipper specifically reduces the expression level of miR-221 in cells.
Figure 8:
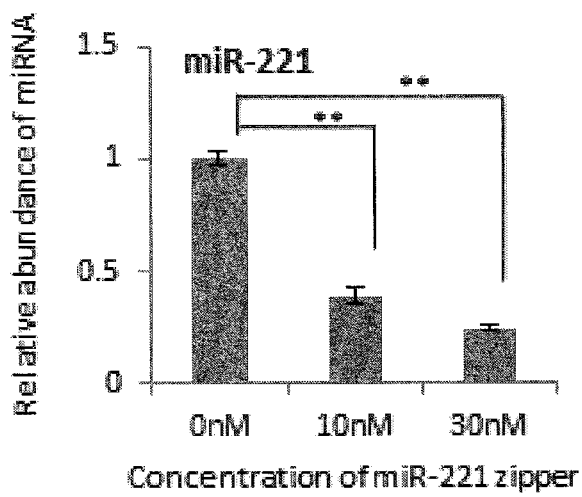
FIG. 8 shows that in one embodiment, the inhibition effect of microRNA-221 zipper on miR-221 is related to concentration.

The result was shown in FIG. 6 that the intracellular level of target miRNA-221 was reduced by about 70-80% after microRNA-221 zipper was transfected into cells at a concentration of 30 nM for 24 hours, and this function was positively correlated with the concentration of microRNA zippers within a certain range (FIG. 8).

In addition, the effect of let-7a zipper on the abundance of let-7a, let-7b and let-7c was examined in breast cancer cell line MDA-MB-231.

Figure 7:
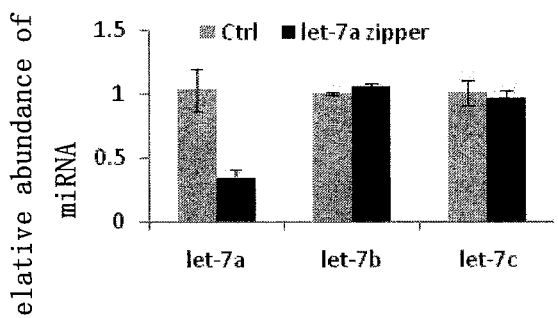
FIG. 7 shows that in one embodiment, the microRNA let-7a zipper specifically reduces the expression level of let-7a in cells, but has no effect on the let-7 family members, let-7b and let-7c with high homology, indicating the specificity of the RNA zipper function.

As shown in FIG. 7, the result showed that the intracellular level of target let-7a was reduced by about 70-80% after let-7a zipper was transfected into cells at a concentration of 30 nM for 24 hours, but did not affect the expression of the homologous let-7b and let-7c. The inhibitory effect of the let-7a zipper on the target let-7a was positively correlated with the concentration of the microRNA zipper within a certain range (FIG. 7).

Example 3

Design of microRNA Zipper Junction Region

Figure 9:
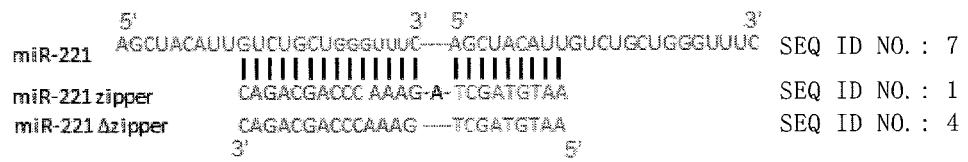
FIG. 9 shows the microRNA-221 zipper structure with two different structures in one embodiment.
Figure 11:
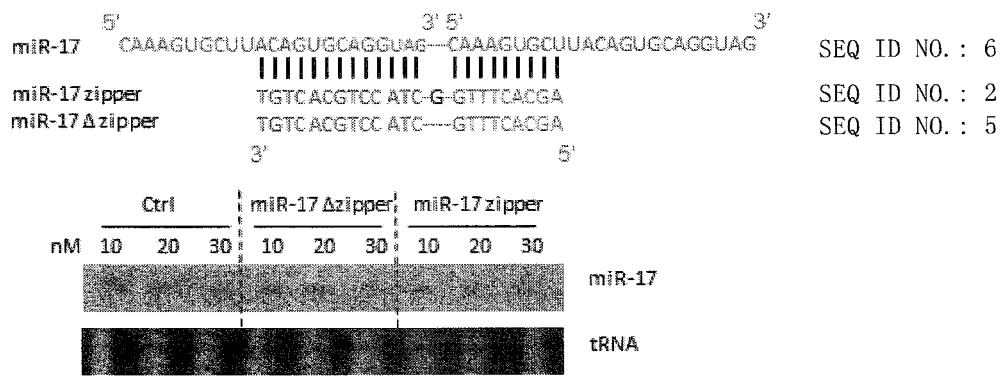
FIG. 11 shows that in one embodiment, the effect of the miR-17 zipper with one nucleotide residue attached to the first binding region and the second binding region is significantly better than that of the miR-17Δ zipper without the junction region.

In order to optimize the optimal microRNA zipper structure, experiments were designed to verify the need to establish a junction region between the first binding region and the second binding region. The inventors constructed two different structures of zippers, microRNA zippers for miR-221 and miR-17 (FIGS. 9 and 11). In one of them, the first binding region was directly linked to the second binding region, without additional bases, which was called microRNA zippers. Compared with a microRNA zipper with one base as a junction region, the effects of the two structures were compared.

The miR-17 zipper and miR-221 zipper sequences were shown as follows (those with the + sign were the LNA modified base)

```
miR-221 zipper:
                            (SEQ ID NO.: 1)
AA+TGTAGCTAGAAACCCAGCA+GAC miR-221 Δ zipper:
                            (SEQ ID NO.: 4)
AA+TGTAGCTGAAACCCAGCA+GAC;
```

Figure 10:
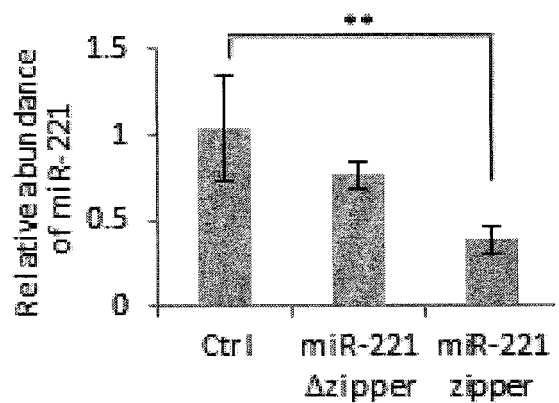
FIG. 10 shows that the effect of the miR-221 zipper with a nucleotide residue attached to the first binding region and the second binding region in the embodiment of FIG. 9 was significantly better than that of the miR-2210 zipper without the nucleotide residues.

As shown in FIG. 10, the effect of microRNA zipper with one base in the junction region is significantly better than that of the microRNA zipper without additional connected bases.

In the same way, the miR-17 zippers with one base and no additional connecting base were synthesized, and the zipper sequences were shown as follows (those with a + sign are LNA modified bases)

```
miR-17 zipper:
                            (SEQ ID NO.: 2)
A+AGCACTTTGGCTACCTGCACT+GT;

miR-17Δ zipper:
                            (SEQ ID NO.: 5)
A+AGCACTTTGCTACCTGCACT+GT;
```

By nucleic acid blot hybridization method, it was confirmed that the effect of the miR-17 zipper with one base in the junction region is superior to that of the miR-17 zipper without additional connecting bases (FIG. 11).

Example 4

Base Selection of microRNA Zipper Junction Region

In order to optimize the structure of the microRNA zipper and verify whether there was difference when different bases were used as nucleotides in the junction region of a microRNA zipper, four different bases of ATCG were respectively used as the connecting bases of the miR-17 zipper as shown in FIG. 2. Four microRNA zippers were constructed to compare the effects of the four structures.

Figure 12:
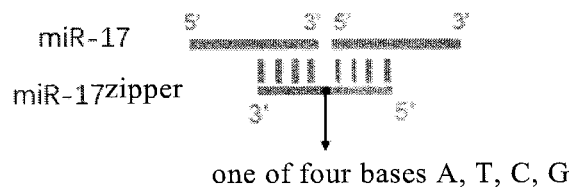
FIG. 12 shows that in one embodiment, the effect of using G and T to connect the first binding region and the second binding region of the microRNA zipper is better than that of using A and C.
Figure 12:
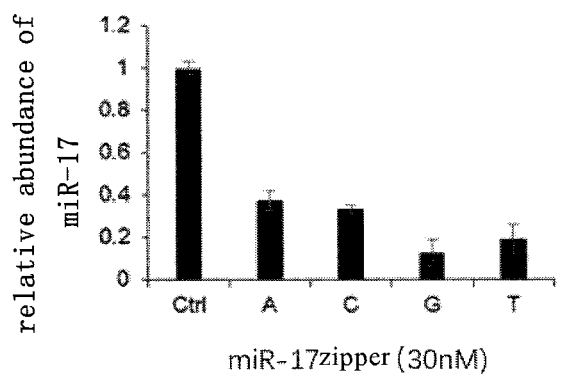

The results were shown in FIG. 12. Different bases of ATCG were used as the connecting nucleotides of the microRNA zipper, indicating that the miRNAs can be knocked down, but the effect of G and T is better than that of A and C, and using G as a connecting nucleotide, the effect of microRNA zipper was optimal.

Example 5

Exploration of the Length of microRNA Zipper Junction Region

In order to optimize the structure of the microRNA zipper, and verify whether the number of nucleotides in the microRNA zipper junction region affects the effect of the microRNA zipper, one, two and three nucleotides were randomly placed at the position of the junction region of the miR-17 zipper as shown in FIG. 2, and three microRNA zippers were constructed to compare the effects of the three structures.

Figure 13:
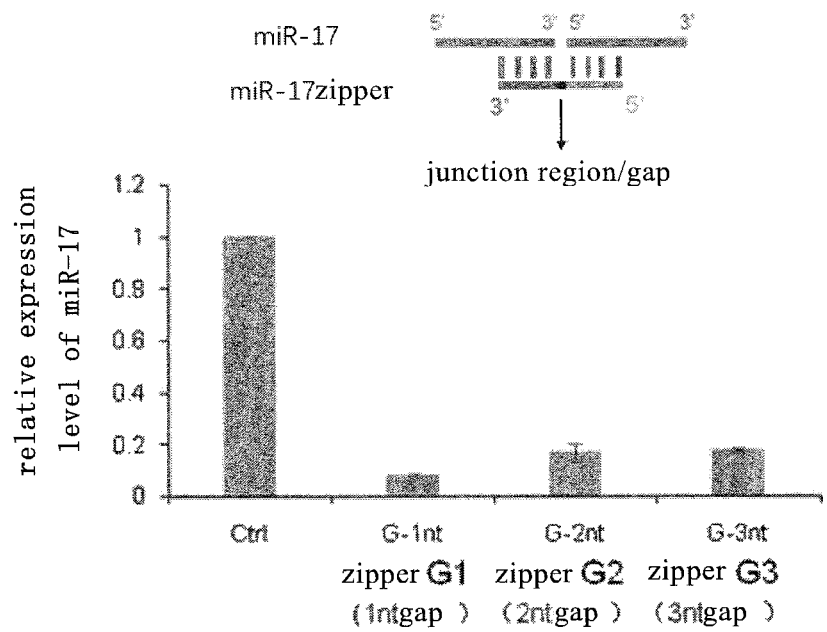
FIG. 13 shows that in one embodiment, the effect of setting 1 nucleotide residue between the first binding region and the second binding region of the microRNA zipper is better than that of setting 2 or 3 nucleotide residues.

The results of one example were as shown in FIG. 13. One nucleotide G, two nucleotides GA, and three nucleotide GCA were randomly placed at the position of the junction region of the microRNA zipper, respectively, indicating that the miRNA can be knocked down. However, the effect of a microRNA zipper with 1 nucleotide junction region is slightly better than that of a small RNA zipper with 2 nucleotides and 3 nucleotides as a junction region.

When more than three nucleotide residues were placed in the junction region of the microRNA zipper, the off-target effect was significantly increased, the non-specificity was increased, and the expression of the target small RNA was difficult to be effectively knocked down and functionally inhibited. Therefore, the junction region is preferably 0-3 nucleotide residues.

In addition, the inventors also attempted to replace 0-3 nucleotide residues with a linker molecule similar in steric hindrance to the 0-3 nucleotide residues, such as amino acid residues, amide groups, hydrocarbyl groups, ether groups, oligosaccharides, and the like. For example, glycine residues, glucosyl groups, methylene groups, etc., can effectively knock down the expression of target small RNA.

Example 6

Variant Design of the Junction Region of the microRNA Zipper

Figure 14:
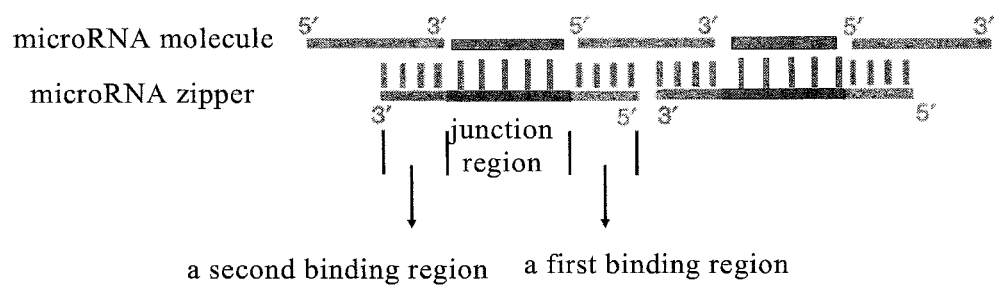
FIG. 14 shows a structural pattern in one embodiment, in which a complete microRNA antisense complementary sequence is placed between the first binding region and the second binding region of the microRNA zipper as the junction region.

In addition to the design of a 0-3 nucleotide residue or a sterically hindered molecule similar to the 0-3 nucleotide residues as a junction region as described in Example 5, the present invention also attempted to introduce the antisense complementary sequence of n microRNA molecules in the junction region, the microRNA molecule was the same as or different from the microRNA targeted by the first binding region or the second binding region, which was as shown in FIG. 14. The antisense complementary sequence of one microRNA molecule was introduced in the junction region. Here, the introduction of the antisense complementary sequence of n microRNA molecules forms an RNA sponge-like function, which can be used to bind a plurality of different microRNA molecules and functionally inhibit a plurality of different microRNA molecules. Preferably, n was an antisense complementary sequence of 1-20 sets of microRNA molecules, wherein each antisense complementary sequence may be separated by 0-3 nucleotide residues.

Figure 15:
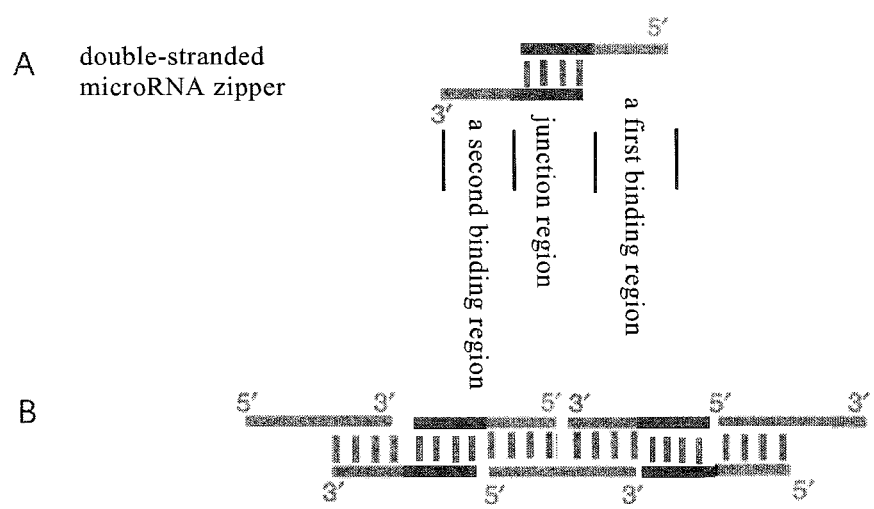
In FIG. 15, element A shows that in one embodiment, the first binding region and the second binding region of the microRNA zipper are located on two oligonucleotide strands, respectively, and the two oligonucleotide strands contain an antisense sequence that can form a complementary pair of bases, such that the junction region of such a small RNA zipper is double-stranded.

The aforementioned junction region and the first binding region and the second binding region of the microRNA zipper were all single-stranded, and the inventors had also attempted to design a double-stranded junction region structure, as shown in FIG. 15. The double strand of the junction region was formed by combining the first binding region and the partial sequence of second binding region by an antisense complementary sequence. In order to ensure the stability of the junction region, the antisense complementary sequence located in the junction region needed to form not less than 7 base pairs. It has been experimentally verified that the double-stranded microRNA zipper as shown in FIG. 15 can also effectively knock down the expression of the target small RNA and achieve an inhibitory effect on its function.

Example 7

Design Optimization of the First Binding Region and the Second Binding Region of the microRNA Zipper The structure of the first binding region (N1), the second binding region (N2) of the microRNA zipper as described in Example 1, and the 5' region (N1') of the target small RNA bound by the first binding region, and 3' region (N2') of the target small RNA bound to the second binding region was as shown in Table 1:

TABLE 1

Proportion of nucleotide lengths of the first binding region (N1) and the second binding region (N2)

| microRNA zipper | N1 | N1' | N2 | N2' | N0 |
| --- | --- | --- | --- | --- | --- |
| miR-17 zipper (FIG. 2) | 9 | 10 | 13 | 13 | 23 |
| miR-221 zipper (FIG. 3) | 9 | 9 | 14 | 14 | 23 |
| Let-7a zipper (FIG. 4) | 11 | 11 | 11 | 11 | 22 |

According to Table 1 and FIG. 3, the bases of the first and second binding regions of the miR-221 zipper can be completely matched to those of the 5' or 3' region of the target small RNA, respectively, N1/N0=0.39, N2/N0=0.61;

According to Table 1 and FIG. 4, the bases of the first binding region and the second binding region of the let-7a zipper can be completely matched to those of the 5' or 3' region of the target small RNA, respectively, N1/N0=0.5, N2/N0=0.5;

According to Table 1 and FIG. 2, the base of the second binding region of the miR-17 zipper is completely matched to that of the 3' region of the target small RNA, and the base of the first binding region of the miR-17 zipper was not exactly matched to that of the 5' region of the target small RNA. It can be seen from FIG. 2 that a base deletion occurred at the end of the first binding region, and the expression of the targeted microRNA can be effectively suppressed, wherein N1/N0=0.39, N2/N0=0.56.

In another embodiment, an attempt was made to vary the nucleotide lengths of the first binding region and the second binding region. Only when N1:N0=(0.3–0.7):1 and N2:N0=(0.3–0.7):1 were satisfied, the microRNA zipper can effectively connect the microRNAs end to end to form a stable double-stranded structure; and there were two extreme cases: (1) N1:N0=0.3, and N2:N0=0.3; 2) N1:N0=0.7, and N2:N0=0.7, both of which can inhibit the expression of the targeted small RNA.

In another embodiment, an attempt was made to remove a base at the free end of the first binding region or the second binding region, such as a deletion of a base as shown in FIG. 2, at the free end of the first binding region or the second binding region. Up to two bases can be tolerated for the deletion, and the microRNA zipper can effectively connect the microRNAs end to end to form a stable double-stranded structure.

In another embodiment, an attempt was made to randomly remove bases within the first binding region or the second binding region chain, and up to two bases can be tolerated for the deletion in the first binding region or the second binding region.

A bulge or bump can be formed in the targeted RNA region, and a stable double-stranded-like structure can also be formed.

In another embodiment, an attempt was made to add redundant bases at the free ends of the first binding region or the second binding region, the redundant bases were unable to form a base complementary pairing on the targeted microRNA strand, the addition of up to two bases were allowed at the free end of the first binding region or the second binding region, and a stable double-stranded-like structure can also be formed.

In another embodiment, an attempt was made to add redundant bases within the first binding region or the second binding region, the redundant bases were unable to form a base complementary pairing on the targeted microRNA strand, up to two bases can be tolerated for the addition in the first binding region or the second binding region chain. A bulge or bump can be formed in the microRNA zipper region, and a stable double-stranded-like structure can also be formed.

In another embodiment, an attempt was made to modify the type of base within the strand of the first binding region or the second binding region, the modified base was unable to form a base complementary pairing on the targeted microRNA strand, up to two bases can be tolerated for the modification in the first binding region or the second binding region chain, a bulge or bump can be formed in the microRNA zipper region, and a stable double-stranded-like structure can also be formed.

All of the above embodiments are not limited to the microRNA zipper sequences disclosed in the present invention, and any inhibitor of microRNA can be designed with reference to the above embodiments, and the targeted microRNAs are not limited to miRNAs, and may also include piRNAs or siRNAs.

Example 8

Base Modification of microRNA Zipper

Not only deoxyribonucleic acid, but also ribonucleic acid, as well as modified stable bases can be used in microRNA zippers. The modified base can avoid the self-binding of the microRNA zipper and enhance the binding specificity between the microRNA zipper and the target microRNA. In addition to the LNA modification described in Examples 1-3, the microRNA zipper can also be modified with 2'-MOE, 2'-Fluoro, PNA, morpholino, and ZEN to further improve the stability of the microRNA.

Example 9

The Improvement of Drug Sensitivity in Tumor Cells by MicroRNA Zippers

Figure 16:
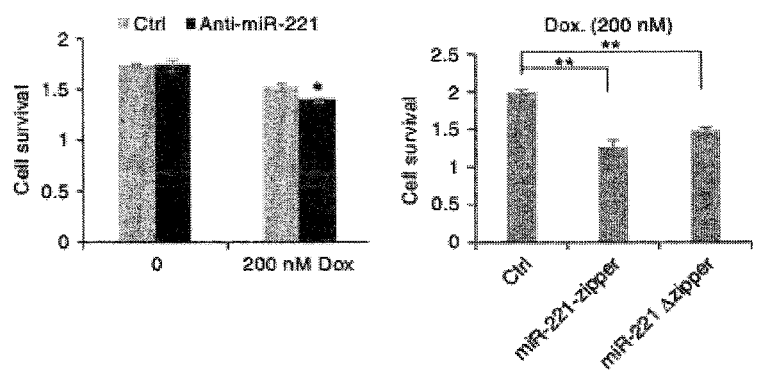
FIG. 16 shows that in one embodiment, MDA-MB-231 cells treated with miR-221 zipper show an increase in sensitivity to doxorubicin (Dox): the left panel shows that, after the treatment of the antisense nucleic acid of miR-221 (Anti-miR-221), cell viability of MDA-MB-231 cells is shown for 200 nM doxorubicin; the right panel shows cell viability after the treatment of miR-221 zipper and miR-221Δ zipper.

MDA-MB-231 cells were not sensitive to the chemotherapy drug doxorubicin (Dox). After transfecting the miR-221 zipper into MDA-MB-231 cells, 200 nM doxorubicin was added. Upon transfection, sensitivity of MDA-MB-231 cells to doxorubicin (Dox) was increased. As shown in FIG. 16, the left panel showed the cell viability of MDA-MB-231 cells on 200 nM doxorubicin after treatment with antisense nucleic acid (Anti-miR-221) of miR-221; the right panel showed the cell viability after the treatment with the miR-221 zipper and the miR-221Δ zipper as described in Example 3. It can be obviously seen that cells treated with miR-221 zipper and miR-221Δ zipper showed higher sensitivity to doxorubicin relative to those treated with the same concentration of anti-miR-221.

All publications mentioned herein are incorporated by reference as if each individual document was cited as a reference, as in the present application. It should also be understood that, after reading the above teachings of the present invention, those skilled in the art can make various changes or modifications, equivalents of which falls in the scope of claims as defined in the appended claims.

The invention claimed is:

1. A small RNA inhibitor comprising a first binding region and a second binding region; the first binding region is located at 5' end of the small RNA inhibitor, comprising an antisense complementary sequence targeting a 5' region of a small RNA, which can bind to the 5' region of the targeted small RNA molecule by base complementation; the second binding region is located at 3' end of the small RNA inhibitor, comprising an antisense complementary sequence targeting a 3' region of the small RNA, which can bind to the 3' region of the targeted small RNA molecule by base complementation, wherein a length of the small RNA inhibitor sequence is 19-26 nt; there is a junction region between the first binding region and the second binding region, the junction region is composed of 0-3 nucleotide residues, the junction region and the first binding region and the second binding region are single-stranded; the small RNA inhibitor can bind the small RNA molecule, thereby inhibiting biological functions of the small RNA molecule, the type of small RNA molecule is selected from the group consisting of:

miRNA, siRNA, and piRNA; and a length of nucleotide contained in the first binding region is N1, a length of nucleotide contained in the second binding region is N2, a length of nucleotide in the 5' region of the small RNA molecule is N1', a length of nucleotide in the 3' region of the small RNA is N2', a length of total nucleotides of the small RNA is N0, and the 5' region of the small RNA molecule does not overlap with the 3' region of the small RNA molecule, wherein $N1'+N2'=N0$;

$0.3<N1'/N0<0.7$;

$0.3<N2'/N0<0.7$;

$N1:N0=(0.3~0.7):1$; and $N2:N0=(0.3~0.7):1$;

wherein a ratio of the length N1 of the first binding region and the length N2 of the second binding region to the total nucleotide length N0 of the small RNA molecule is $N1:N0=(0.4~0.6):1$, $N2:N0=(0.4~0.6):1$;

bases of the first binding region or the second binding region are completely complementary binded to all bases of the 5' region or the 3' region of the small RNA molecule.

2. The small RNA inhibitor of claim 1, wherein the junction region comprises one nucleotide residue selected from a group consisting of: A, T/U, G and C.

3. The small RNA inhibitor of claim 2, wherein the nucleotide residue in the junction region is G or T.

4. The small RNA inhibitor of claim 1, wherein nucleotide residues of the first binding region and the second binding region contain modified bases.

5. The small RNA inhibitor of claim 4, wherein the modified bases comprise LNA, 2'-OMe or 2'-MOE.

6. A pharmaceutical composition comprising: (a) a small RNA inhibitor of claim 1, and b) a pharmaceutically acceptable carrier.

7. A kit comprising (a) a small RNA inhibitor of claim 1, and b) a biologically acceptable carrier.

* * * * *